US009320651B2

(12) United States Patent
Packard et al.

(10) Patent No.: US 9,320,651 B2
(45) Date of Patent: Apr. 26, 2016

(54) SURGICAL KNIFE HANDLE AND KNIFE

(75) Inventors: Richard Packard, Bracknell (GB); Simon Checkley, Bromsgrove (GB); Ian Hutchinson, Chinnor (GB)

(73) Assignees: Core Surgical Limited, Oxfordshire (GB); e-Medix Limited, Birmingham (GB)

( * ) Notice: Subject to any disclaimer, the term of this patent is extended or adjusted under 35 U.S.C. 154(b) by 533 days.

(21) Appl. No.: 13/393,599

(22) PCT Filed: Sep. 10, 2009

(86) PCT No.: PCT/GB2009/051164
§ 371 (c)(1),
(2), (4) Date: Apr. 9, 2012

(87) PCT Pub. No.: WO2011/030081
PCT Pub. Date: Mar. 17, 2011

(65) Prior Publication Data
US 2012/0191114 A1    Jul. 26, 2012

(51) Int. Cl.
*A61F 9/013*    (2006.01)
*A61B 17/3211*    (2006.01)

(52) U.S. Cl.
CPC ........... *A61F 9/0133* (2013.01); *A61B 17/3211* (2013.01); *A61B 2017/32116* (2013.01)

(58) Field of Classification Search
CPC ........... A61B 17/3211; A61B 17/3213; A61B 2017/32116; A61F 9/00736; A61F 9/0133
USPC .............................. 606/167, 170; 30/329, 337
See application file for complete search history.

(56) References Cited

U.S. PATENT DOCUMENTS

| 1,100,394 | A | * | 6/1914 | Parker | 30/339 |
| 1,706,712 | A | | 3/1929 | Sklar | |
| 1,725,047 | A | | 8/1929 | Behrman | |
| 2,482,385 | A | * | 9/1949 | Urban et al. | 279/56 |
| 3,262,205 | A | * | 7/1966 | Arden | 30/338 |
| 3,798,688 | A | | 3/1974 | Wasson | |
| 4,324,044 | A | * | 4/1982 | Shahinian, Jr. | 30/294 |
| 4,516,575 | A | | 5/1985 | Gerhard et al. | |
| 4,693,245 | A | * | 9/1987 | Pao | 606/107 |
| 4,730,613 | A | | 3/1988 | Gordy | |
| 4,815,218 | A | | 3/1989 | Gordy | |
| 5,554,137 | A | * | 9/1996 | Young et al. | 604/264 |
| 5,658,303 | A | | 8/1997 | Koepnick | |

(Continued)

FOREIGN PATENT DOCUMENTS

JP    S59-172407 U    11/1984
WO    WO 94/09710    5/1994

OTHER PUBLICATIONS

Mar. 10, 2012 International Preliminary Report on Patentability.

(Continued)

*Primary Examiner* — Alexander Orkin
(74) *Attorney, Agent, or Firm* — Hahn Loeser & Parks LLP

(57) ABSTRACT

A surgical knife handle comprising a handle body (102) and a blade receiving portion (104) defined at a first end of the handle body, which blade receiving portion comprises a blade receiving bore and a blade support (118) extending to a first side of the blade receiving bore. A surgical knife comprising a handle, a blade defined at a first end of the handle and a blade support extending to a first side of the blade.

12 Claims, 6 Drawing Sheets

(56) References Cited

U.S. PATENT DOCUMENTS

| | | | |
|---|---|---|---|
| 5,792,162 A * | 8/1998 | Jolly et al. | 606/167 |
| 6,099,543 A * | 8/2000 | Smith | 606/167 |
| 6,139,560 A * | 10/2000 | Kremer | 606/166 |
| 6,506,199 B2 * | 1/2003 | Rogers et al. | 606/172 |
| 2002/0161387 A1 * | 10/2002 | Blanco | 606/185 |
| 2004/0181950 A1 | 9/2004 | Rodgers et al. | |
| 2005/0070941 A1 * | 3/2005 | Isogimi | 606/166 |
| 2006/0041265 A1 * | 2/2006 | Shackelford | 606/167 |
| 2008/0319463 A1 * | 12/2008 | Hickingbotham | 606/161 |

OTHER PUBLICATIONS

Sep. 24, 2013 Office Communication in connection with prosecution of JP 2012-528437, (English translation).

Office Communication in connection with prosecution of CN 2009-80161407.X, (English translation).

* cited by examiner

SURGICAL KNIFE HANDLE AND KNIFE

CROSS-REFERENCE TO RELATED APPLICATIONS

The present application is a submission under 35 U.S.C. §371 of International Application No. PCT/GB2009/051164, filed on 10 Sep. 2009, and published in the English language on 17 Mar. 2011 with publication no. WO 2011/030081.

BACKGROUND

The present invention is concerned with a surgical knife handle and knife. More specifically, the present invention is concerned with a surgical knife handle and knife comprising a blade support structure for supporting a knife blade projecting from a blade handle.

Eye surgery, such as cataract removal is performed using specialist knives. Such knives are constructed having a handle portion for the surgeon to grip and a blade projecting therefrom to perform the incision. Generally, the handle is substantially cylindrical having a main axis. The blade projects from the handle substantially in the direction of the main axis.

Often, it is desirable to provide such a knife with separate blade and handle components. For example, the handle can be constructed from a plastics material with a root of the blade embedded therein such that a portion of the blade projects from the handle portion.

If flat blades are used, it is desirable to provide a blade with as thinner cross section as possible. Thin blades provide a cleaner cut. The problem with this is that thinner blades can flex more easily. The point at which the blade projects from the handle portion acting as a fulcrum. This flexion detrimentally affects the control that the surgeon has over the path of the blade during the incision. This is clearly undesirable.

BRIEF SUMMARY

It is an aim of the present invention to provide an improved knife blade and knife.

According to a first aspect of the present invention, there is provided a surgical knife handle comprising a handle body and a blade receiving portion defined at a first end of the handle body, which blade receiving portion comprises a blade receiving bore and a blade support extending to a first side of the blade receiving bore.

According to a second aspect of the present invention there is provided a surgical knife comprising a handle, a blade defined at a first end of the handle and a blade support extending to a first side of the blade.

By providing a blade support on a side of the blade as it projects from the handle, the blade can be supported and the amount of flexion experienced by the blade is reduced. As such, the precision with which the surgeon can make his incision is greatly increased.

An example knife handle and knife will now be described with reference to the accompanying drawings in which:—

DETAILED DESCRIPTION

Figure 1:
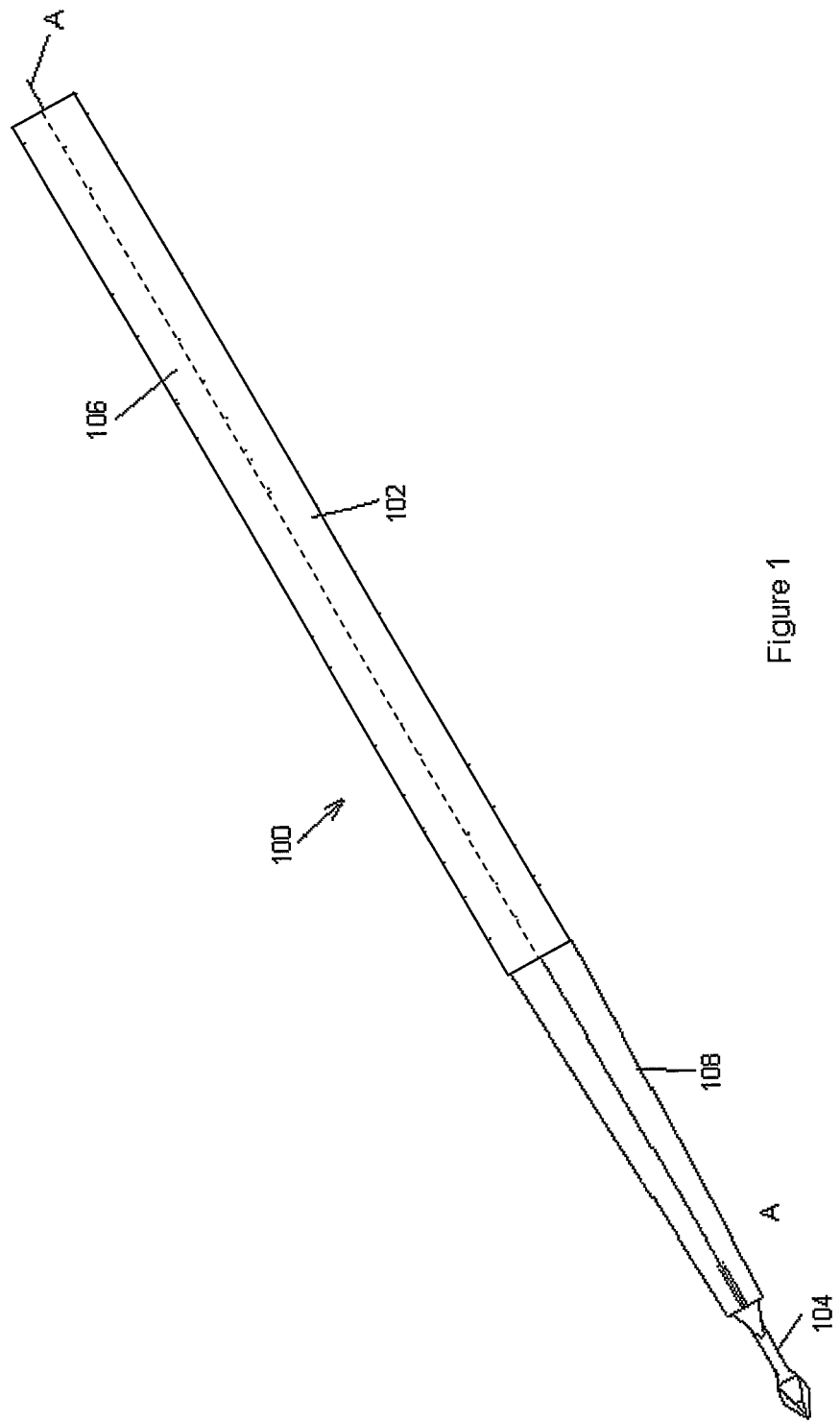
FIG. 1 is a perspective view of a knife in accordance with the present invention.

Referring to FIG. 1, a surgical knife 100 comprises a handle 102 and blade component 104.

The handle 102 comprises a cylindrical portion 106 and a gently tapering frusto-conical portion 108 extending therefrom. The handle 102 defines a main axis A through its longitudinal centre.

Figure 2:
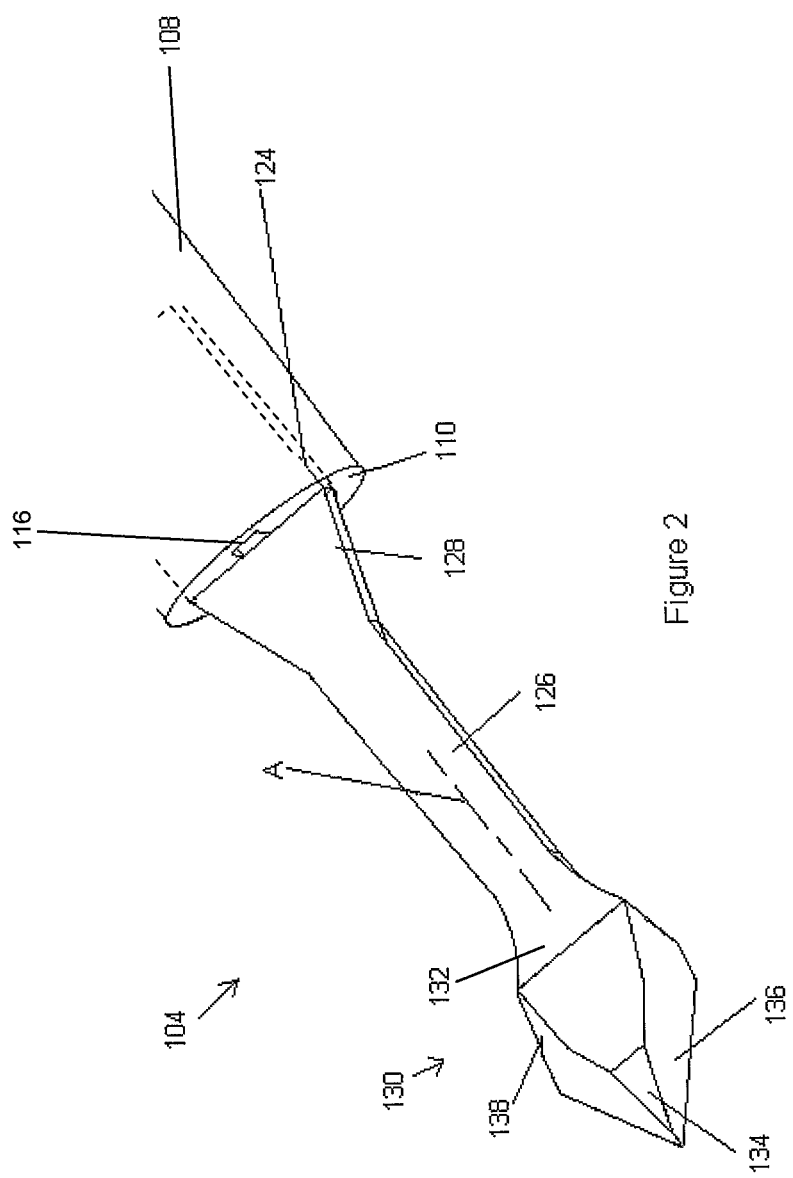
FIG. 2 is a close-up view of a part of the knife of FIG. 1.
Figure 3:
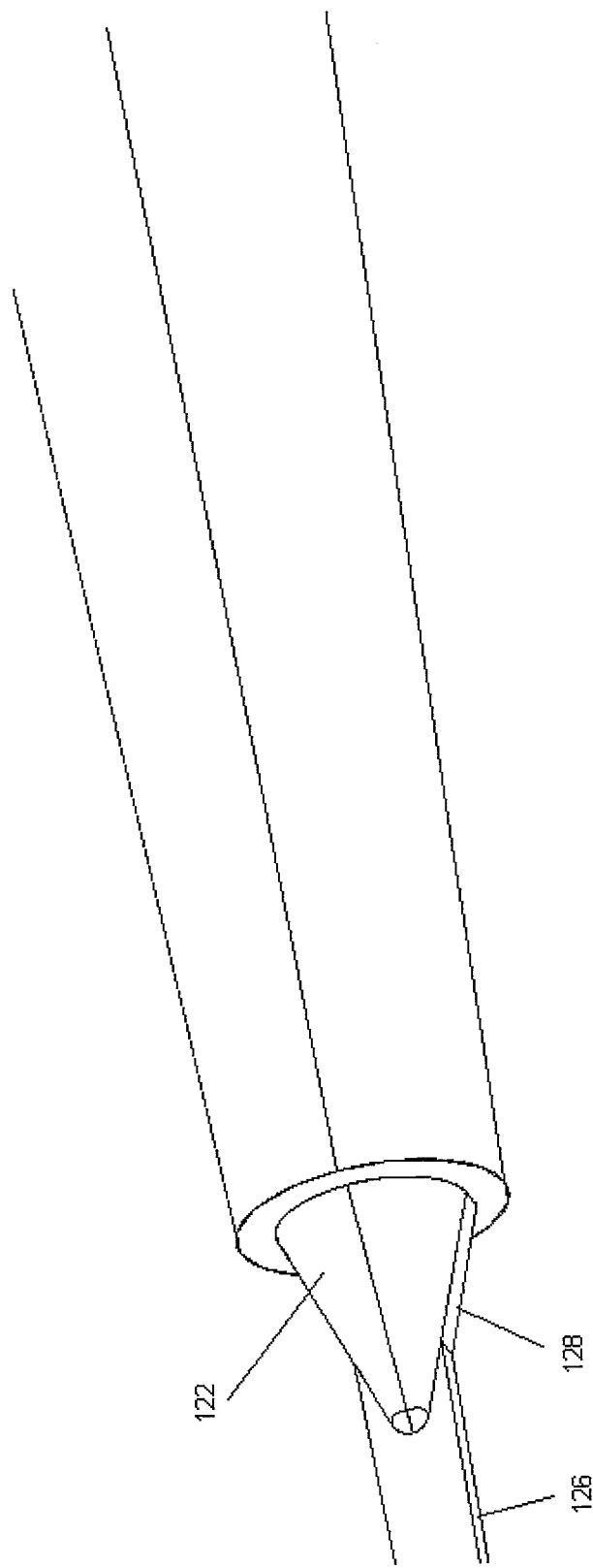
FIG. 3 is a close-up view of the underside of a part of the knife of FIG. 1.
Figure 4:
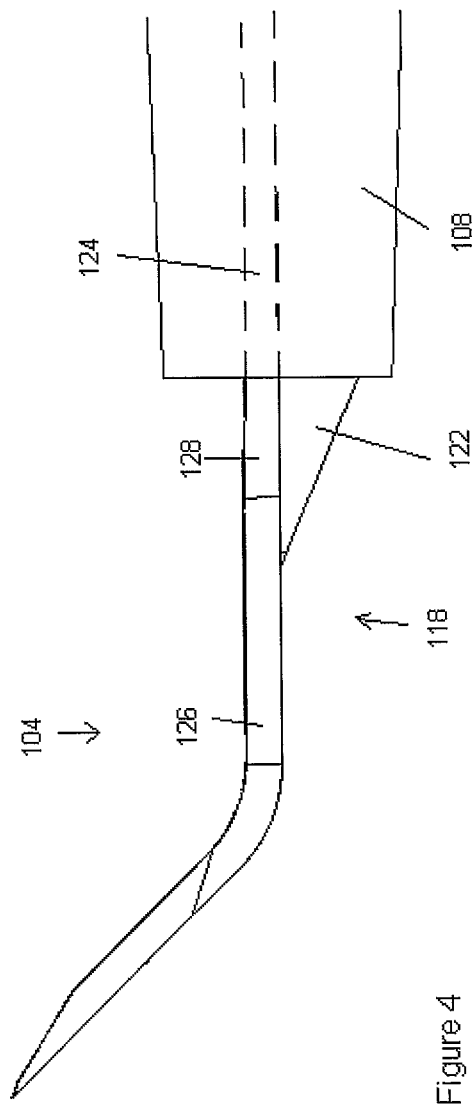
FIG. 4 is a side view of a part of the knife of FIG. 1.
Figure 5:
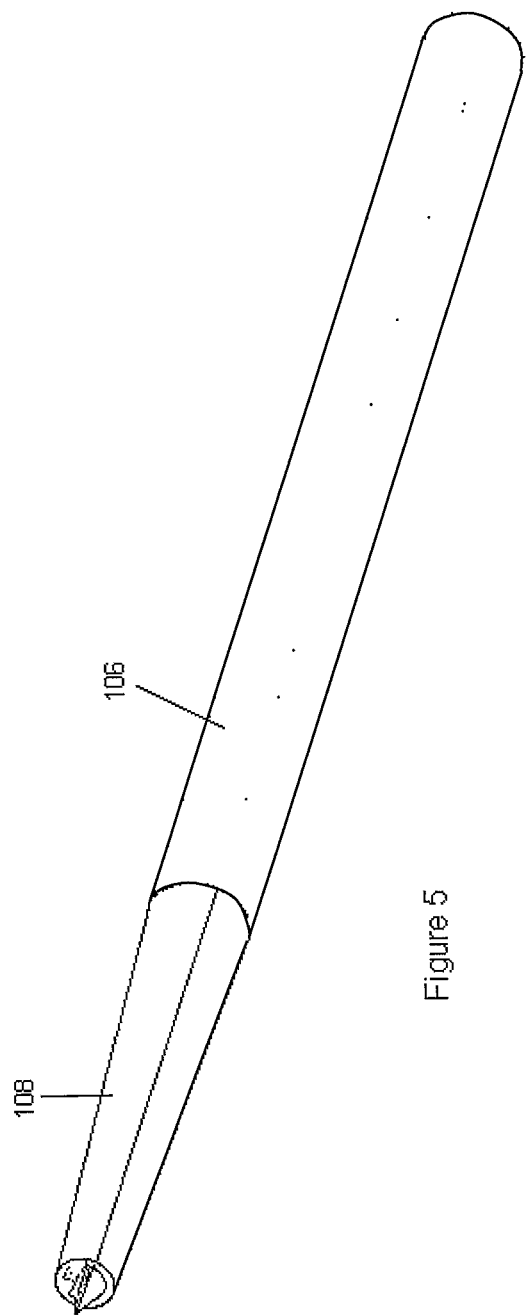
FIG. 5 is a perspective view of the handle of the knife of FIG. 1 without the blade.
Figure 6:
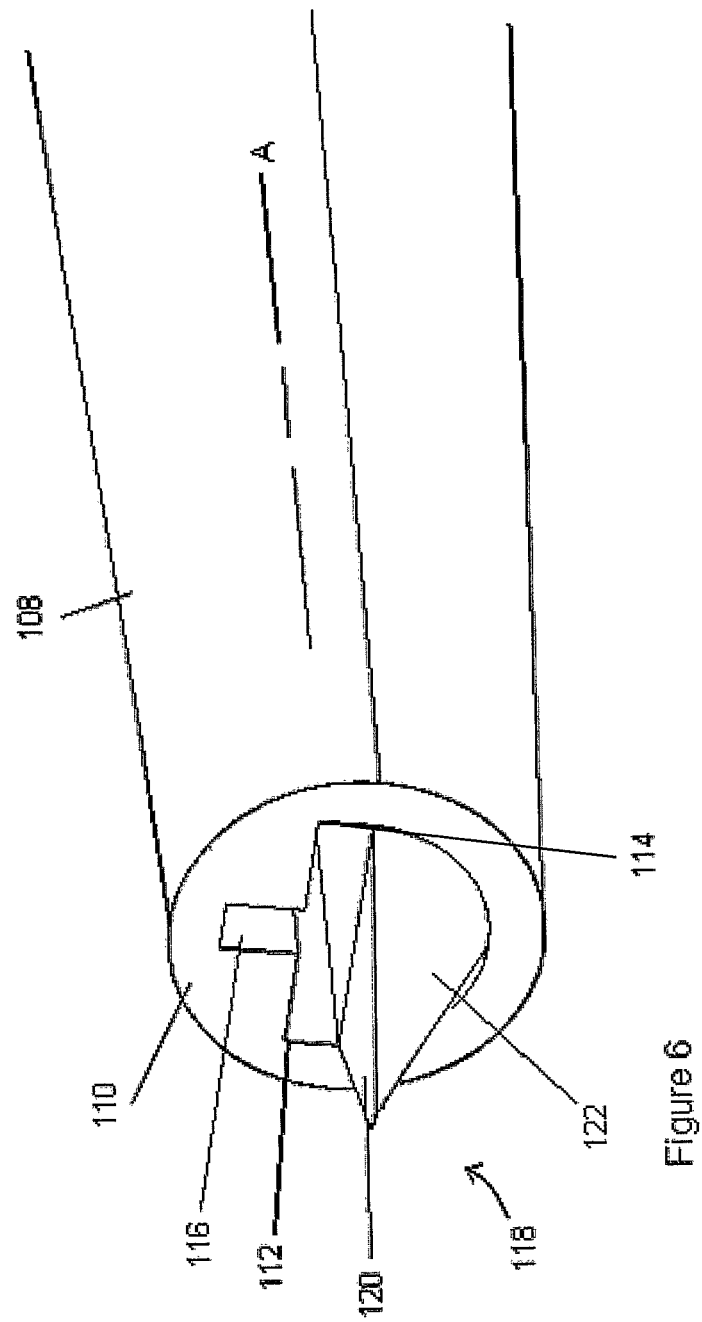
FIG. 6 is a close-up view of a part of the handle of FIG. 5.

Turning to FIG. 2, at the end of the frusto-conical portion 108 opposite the cylindrical portion 106, there is provided a face 110 defined perpendicular to the axis A. As can be seen in FIG. 6, the face 110 comprises a T-shaped bore 112 extending into the handle 102 parallel to the axis A. The T-shaped bore 112 comprises an elongate slot 114 and a projecting leg 116 at right angles thereto.

The T-shaped bore is 112 is provided such that the male mould tool used to form the bore 112 is structurally inflexible.

The handle 102 further defines a blade support member 118 projecting from the face 110, away from the frusto-conical portion 108 and in a direction generally parallel with axis A. The blade support member 118 is defined by a flat planar blade support surface 120 and a semi-conical surface 122. The blade support surface 120 extends from an edge of the elongate portion 114 of the T-shaped bore 112. It will be noted that the part of the face 110 opposite the blade support member 118 is flush with the bore 112. Specifically, the blade support member 118 extends only on a single side of the blade component 104.

The blade component 104 comprises a blade root 124 which is generally rectangular and tapers into a blade neck 126 via a tapered portion 128. The narrow blade neck 126 assists the user's visibility in use.

The blade component 104 further comprises a cutting head 130 as shown in FIG. 2. The cutting head 130 comprises a neck 132 which extends and widens from the neck portion 126. The cutting head 130 comprises a pointed tip 134, a first bevelled portion 136 and a second bevelled portion 138. The second bevelled portion 138 is bevelled at a shallower angle to the axis A than the first bevelled portion 136. As such, upon insertion of the knife into the patient's cornea, once the first bevelled portion 138 has been inserted, a change in resistance can be felt by the surgeon and the angle of insertion altered in order to provide the desired cut.

When the knife 100 is assembled, the root 124 of the blade 104 is inserted into the T-shaped bore 112 such that a bottom face of the tapered portion 128 and the neck 126 abuts the blade support surface 120. The blade is secured in the handle in a known fashion (e.g. adhesive).

As mentioned above, in use the surgeon often needs to change the angle of the knife blade relative to the user's eye. In order to prevent flexion of the blade, and hence inhibition of the feedback required in the transition from the first to the second bevelled portion of the cutting head 130 of the blade 104, the blade support member inhibits flexion to allow better control.

It will be noted that the tapering of the blade support member 118 allows it to remain obscured by the blade 104 as shown in FIG. 2. Therefore the blade support member 118 does not obscure the surgeon's view when looking down on their knife as viewed in FIG. 2.

It will also be noted that the reaction force required by the blade support member approaching its tip decreases because the distance to the fulcrum (at the point at which the blade component 104 projects from the surface 110) is increasing. Therefore, tapering the blade support member 118 provides the optimum use of material in supporting the blade.

It will be noted that the handle 102 can be used with a variety of blades which can be inserted into the bore 112.

Variations of the above embodiment will fall within the scope of the present invention.

The above advantages can be achieved with a single piece handle and blade (e.g. machined from metal block material).

The surface 122 of the blade support member need not be frusto-conical. The surface may be flat, polygonal, or any other appropriate shape. The blade support member may not be tapered, however, this is not preferred as a non tapered support member would not be as mechanically efficient and may obscure the surgeon's view.

The invention claimed is:

1. A surgical knife comprising:
   a blade component comprising a blade neck having a first side and a second side opposite to the first side, and a cutting head extending from the second side of the blade neck at an angle of less than 180° relative to the second side of the blade neck;
   a handle body, having a blade receiving bore in a face at a first end of the handle body, the blade component being embedded in the blade receiving bore proximate the blade neck; and
   a blade support extending from the face along and adjacent to the first side of the blade neck and supporting the blade neck, the blade support being defined by the handle body extending further on a first side of the blade receiving bore than on a second side of the blade receiving bore, and the blade support having an outside surface;
   wherein a closed perimeter distinct from the blade support, that is entirely on the face, defines the second side of the blade receiving bore and defines where the outside surface of the blade support extends from the face.

2. A surgical knife according to claim 1 in which the handle body on the second side of the blade receiving bore is substantially flush with the blade receiving bore.

3. A surgical knife according to claim 2 in which the blade support tapers away from the blade receiving bore.

4. A surgical knife according to claim 1 in which the blade support tapers away from the blade receiving bore.

5. A surgical knife according to claim 4 in which the outside surface of the blade support is a semi-frustoconical surface.

6. A surgical knife according to claim 1 in which the blade support defines a flat, planar blade support surface opposite the outside surface of the blade support.

7. A surgical knife according to claim 1 in which the handle body defines a main axis, and in which the face is defined by a planar surface at an angle to the main axis.

8. A surgical knife according to claim 7 in which the planar surface is perpendicular to the main axis.

9. A surgical knife according to claim 1 in which the blade component defines a cutting edge on a first bevelled portion and a second bevelled portion, wherein the bevelled portions are bevelled at different angles.

10. A surgical knife according to claim 9 in which the second bevelled portion is closer to the handle body than the first bevelled portion and is bevelled at a shallower angle to a central axis of the handle body than the first bevelled portion.

11. A surgical knife according to claim 1 wherein the blade component is secured to the handle body with an adhesive.

12. A surgical knife according to claim 1, wherein the handle body is integral with the blade component.

* * * * *